United States Patent [19]

Petersen et al.

[11] 4,200,512
[45] Apr. 29, 1980

[54] ELECTROCHEMICAL DETECTION OF PHOSGENE IN GAS MIXTURES

[75] Inventors: Otto Petersen; Hans-Dieter Schmidt, both of Krefeld, Fed. Rep. of Germany

[73] Assignee: Bayer Aktiengesellschaft, Leverkusen, Fed. Rep. of Germany

[21] Appl. No.: 804,696

[22] Filed: Jun. 8, 1977

[30] Foreign Application Priority Data

Jun. 18, 1976 [DE] Fed. Rep. of Germany ....... 2627487

[51] Int. Cl.² ............................................. G01N 27/46
[52] U.S. Cl. .................................. 204/195 R; 204/1 T
[58] Field of Search ............ 204/195 R, 195 P, 195 M

[56] References Cited

U.S. PATENT DOCUMENTS

| 2,757,132 | 7/1956 | Northrop | 204/1 B |
| 3,038,848 | 6/1962 | Brewer et al. | 204/195 R |
| 3,234,117 | 2/1966 | Rost et al. | 204/195 R |
| 3,743,589 | 7/1973 | Nicholas | 204/195 R |
| 3,859,191 | 1/1975 | Frant et al. | 204/195 P |
| 4,049,503 | 9/1977 | Becker et al. | 204/195 R |

OTHER PUBLICATIONS

Blue et al., "Transactions of the Electrochemical Society", vol. LXIII, (1933), pp. 231-238.

*Primary Examiner*—T. Tung
*Attorney, Agent, or Firm*—Sprung, Felfe, Horn, Lynch & Kramer

[57] ABSTRACT

An electrochemical cell having a polarographic device and preferably containing formamide as electrolyte is suitable for detecting very small quantities of phosgene in a gas mixture. Water, sodium acetate and thickener may be added to the electrolyte.

6 Claims, 1 Drawing Figure

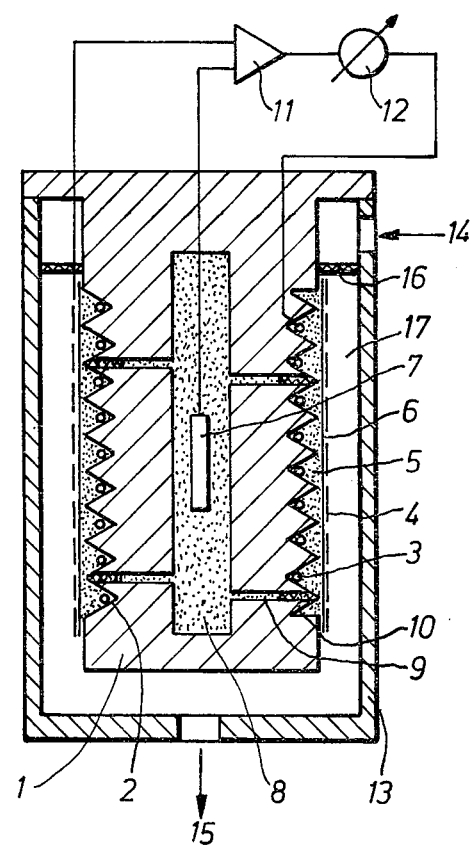

ELECTROCHEMICAL DETECTION OF PHOSGENE IN GAS MIXTURES

This invention relates to a polarographic process for the measurement of phosgene in a gas mixture, in particular for the detection of traces of phosgene in air, and to an apparatus for carrying out this process.

Polarographic arrangements for detecting gases are already known. They are relatively uncomplicated and reliable in operation. The quantitative method of detection is particularly important for environmental protection. The physical changes and changes in composition should be measured as far as possible continuously. A gas detector operating by the polarographic process usually contains a cell with three electrodes. The stability and sensitivity of such a cell are higher than that of a two-electrode arrangement, as is described in German Offenlegungsschriften Nos. 2,155,935 and 2,354,149, but this polarographic method of measurement has the disadvantage of not being sufficiently selective. In many cases it cannot be foreseen what gases are liable to occur in a gas mixture, but it is generally necessary to determine the concentration of a particular gas. The presence of oxides of nitrogen, for example, simulates an excessively high carbon monoxide content, while the sensitivity of detection of phosgene is affected by various constituents such as sulphur dioxide, gases which form chlorine ions, and others.

In German Offenlegungsschrift No. 2,155,935 it is mentioned that if several gases are present in a gas mixture, measures must be provided for detecting and determining the various impurities separately. It is said that this may be achieved by passing the air sample successively through individual cells in each of which only one impurity reacts while the other impurities are inert. The anode and cathode materials, electrolyte and temperature of the electrolyte should be suitably chosen for this purpose. The said Offenlegungsschrift contains no indication as to how phosgene could be detected in small quantities in a gas mixture.

An apparatus which is said to be suitable for detecting hydrocyanic acid, hydrogen sulphide and chlorine gas is available on the market. Its electrolyte must be continuously renewed and its sensitivity of detection is affected by the presence of other gases, for example sulphur dioxide. This apparatus is not suitable for the detection of phosgene.

It is an object of this invention to provide a reliable, highly sensitive and convenient gas detector for phosgene.

The problem is reduced or substantially solved by a polarographic process in which phosgene reacts with the electrolyte and the polarographic detection of the reaction product is not affected by other gases in the gas mixture.

A particularly suitable electrolyte for this process is formamide, which reacts with phosgene according to the equation:

$$COCl_2 + HCO\text{-}NH_2 = HCN + CO_2 + 2\ HCl,$$

so that HCN is detected selectively.

One particular advantage of this arrangement is the high sensitivity of measurement for HCN, which is not deleteriously affected by the presence of other gases such as carbon monoxide, sulphur dioxide, gaseous hydrogen chloride or oxides or nitrogen.

The electrolyte may contain water and sodium acetate. In particular, the sensitivity is improved by the presence of from 0 to 15%, preferably 10%, by weight of water and from 5 to 20%, preferably 20%, by weight of sodium acetate. The electrolyte may be thickened by means of unreactive substances, for example methyl cellulose. Continuous renewal of the electrolyte is unnecessary. The structure of the gas detector is therefore very compact.

An example of the invention is described below with reference to the drawing. The auxiliary electrode 3 is placed in a screw thread 2 cut into a cylindrical body 1 of polypropylene. A mesh wrapped round the threaded part of the cylinder 1 serves as working electrode 4. The electrolyte 5 between the auxiliary electrode 3 and working electrode 4 is thickened. An electrolyte-permeable foil 6 placed on the inside of the working electrode 4 serves both to stabilise the electrolyte mechanically and to reduce the effective quantity of electrolyte, thereby improving the time factor. The reference electrode 7 is placed centrally and dips into the electrolyte 8 which has the same composition as electrolyte 5 but without the thickener. Electrolyte 8 is electrically connected to the thickened electrolyte 5 by channels 9 between the working electrode 4 and auxiliary electrode 3. Each channel 9 contains a diaphragm 10 which prevents the outflow of electrolyte 8 but permits fresh electrolyte to be supplied through it so that the external electrolyte 5, which is thickened, maintains its composition for a long time. The voltage of the polarographic stage of the gas which is to be detached is peselected on the potentiostat 11. Instrument 12 indicates a current proportional to the concentration. The apparatus 1 is enclosed in a housing 13 provided with a gas inlet 14 and gas outlet 15. An annular frit 16 serves to retain the gas to be measured and, at the same time, allows gas to flow uniformly through the chamber 17.

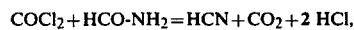

What we claim is:

1. In an apparatus for the polarographic measurement of phosgene in a gas mixture wherein the improvement comprises a polarographic cell containing at least two electrodes and an electrolyte in the cell containing up to 15% by weight of water and formamide which reacts with phosgene to produce a reaction product including HCN the polarographic measurement of which is unaffected by the other gases in the gas mixture whereby a current is obtained which is proportional to the concentration of phosgene.

2. Apparatus as claimed in claim 1 in which the electrolyte contains 10% by weight of water.

3. Apparatus as claimed in claim 2 in which the electrolyte contains from 5 to 20% by weight of sodium acetate.

4. Apparatus as claimed in claim 3 in which the electrolyte contains 20% by weight of sodium acetate.

5. Apparatus as claimed in claim 4 in which the electrolyte is thickened by unreactive substances.

6. Apparatus as claimed in claim 5 in which the electrolyte is thickened with methyl cellulose.